United States Patent [19]

Morita et al.

[11] Patent Number: 5,051,251

[45] Date of Patent: Sep. 24, 1991

[54] HAIR COSMETIC COMPOSITION

[75] Inventors: Kouzi Morita, Funabashi; Toshie Takahashi, Ichikawa; Sachio Naito, Ichikai, all of Japan

[73] Assignee: Kao Corporation, Tokyo, Japan

[21] Appl. No.: 549,027

[22] Filed: Jul. 6, 1990

[30] Foreign Application Priority Data

Jul. 7, 1989 [JP] Japan .................................. 1-176777

[51] Int. Cl.$^5$ ............................................. D61K 7/08
[52] U.S. Cl. ....................................... 424/70; 514/772
[58] Field of Search ...................... 424/70, 47; 514/772

[56] References Cited

U.S. PATENT DOCUMENTS

| | | | |
|---|---|---|---|
| 3,627,824 | 12/1971 | Fujimoto | 562/554 |
| 3,865,542 | 2/1975 | Kalopissis | 424/70 |
| 4,240,450 | 10/1980 | Grollier | 424/71 |
| 4,445,521 | 5/1984 | Grollier | 424/70 |
| 4,711,776 | 12/1987 | Suzuki | 424/47 |
| 4,719,099 | 1/1988 | Grollier | 424/70 |
| 4,910,013 | 3/1990 | Kanamaru | 424/70 |
| 4,931,216 | 6/1990 | Igarashi | 424/70 |

FOREIGN PATENT DOCUMENTS

| | | |
|---|---|---|
| 167382 | 7/1985 | European Pat. Off. . |
| 312992 | 10/1988 | European Pat. Off. . |
| 2345997 | 3/1977 | France . |

OTHER PUBLICATIONS

Patent Abstract of Japan, vol. 1, No. 97, (C-24), Aug. 30, 1977, & JP-A-52 59606, (Kao Sekken K. K.), May 17, 1977.

*Primary Examiner*—Thurman K. Page
*Assistant Examiner*—Susan S. Rucker
*Attorney, Agent, or Firm*—Sughrue, Mion, Zinn, Macpeak & Seas

[57] ABSTRACT

A hair cosmetic composition comprising the following components (A) and (B):

(A) 1.0 to 50.0% by weight, based on the total weight of the composition, of a dialkylene glycol monoalkyl ether represented by formula (I):

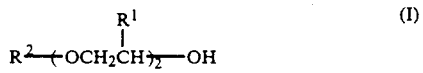

wherein $R^1$ represents a hydrogen atom or a methyl group and $R^2$ represents an alkyl group having 1 to 5 carbon atoms; and (B) 0.01 to 20.0% by weight, based on the total weight the composition, of at least one cationic surfactant is disclosed.

This hair cosmetic composition imparts an excellent texture to the hair and protects the hair from splitting or broken, without showing any stickiness or an oily feel.

3 Claims, No Drawings

HAIR COSMETIC COMPOSITION

FIELD OF THE INVENTION

This invention relates to a hair cosmetic composition. More particularly, it relates to a hair cosmetic which contains a dialkylene glycol monoalkyl ether and a cationic surfactant, and which imparts an excellent texture to the hair and exerts an effect of protecting the hair from damage.

BACKGROUND OF THE INVENTION

Known hair cosmetics contain cationic surfactants such as mono- or di-straight and long chain alkyl quaternary ammonium salts or mono- or di-branched long chain alkyl quaternary ammonium salts in order to improve the texture of the hair. Recently, it has been attempted to use these cationic surfactants together with higher alcohols and fats and oils such as glycerides and liquid paraffin so as to further improve the texture of the hair.

However these known hair cosmetics are disadvantageous in that they give only unsatisfactory effects of improving the texture of the hair. Namely, they are poor in their conditioning effects (for example, softness, moist feel, smoothness, antielectrificating effect) on the hair. Although it has been attempted to add fats and/or oils to hair cosmetics to thereby improve the above-mentioned moist feel, the hair cosmetics thus obtained suffer from some problems, including stickiness and oily feel. These products show limited conditioning effects, in particular, under dry conditions. In addition, known hair cosmetics exert only a limited effect of protecting the hair from damage.

Accordingly, a demand has arisen in the art for a hair cosmetic exhibiting excellent conditioning effects (for example, moist feel) and which will also sufficiently protecting the hair from damage without showing any stickiness or having an oily feel.

Under these circumstances, we have conducted extensive studies in order to overcome the problems of the prior art. As a result, we have found that the combined use of a cationic surfactant with a specific dialkylene glycol monoalkyl ether makes it possible to protect the hair from damage caused by the swelling of the hair upon washing as the dialkylene glycol monoalkyl ether penetrates into the hair and is then adsorbed thereby. We have further found that the hair cosmetic thus obtained exerts excellent conditioning effects (for example, moist feel, softness, smoothness) on the hair without showing any stickiness or having an oily feel even under dry condition, owing to their humecting effect after penetrated into the hair. The present invention was achieved based on these findings.

SUMMARY OF THE INVENTION

The present invention provides a hair cosmetic composition containing the following components (A) and (B):

(A) 1.0 to 50.0 % by weight, based on the total weight of the composition, of a dialkylene glycol monoalkyl ether represented by formula (I):

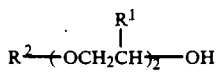

(I)

wherein $R^1$ represents a hydrogen atom or a methyl group and $R^2$ represents an alkyl group having 1 to 5 carbon atoms; and (B) 0.01 to 20.0 % by weight, based on the total weight of the composition, of a cationic surfactant.

DETAILED DESCRIPTION OF THE INVENTION

In the present invention, examples of component (A) represented by the formula (I) include diethylene glycol monomethyl ether, diethylene glycol monoethyl ether, diethylene glycol monopropyl ether, diethylene glycol monobutyl ether, diethylene glycol monopentyl ether, diethylene glycol monoisopropyl ether, diethylene glycol mono-t-butyl ether, dipropylene glycol monomethyl ether, dipropylene glycol monoethyl ether, dipropylene glycol monopropyl ether, dipropylene glycol monobutyl ether dipropylene glycol monopentyl ether, dipropylene glycol monoisopropyl ether and dipropylene glycol mono-t-butyl ether. Among these substances, diethylene glycol monoethyl ether, diethylene glycol monopropyl ether and diethylene glycol monobutyl ether are preferable as component (A).

The dialkylene glycol monoalkyl ether used as component (A) of the present invention may be produced in a conventional manner as described, for example, in *Kesyohin Genryo Kijun* (Standard of Raw material for Cosmetic), published by Yakujinipposya (1984).

The hair cosmetic composition of the present invention may contain 1.0 to 50.0 % (by weight based on the total weight of the composition, the same will apply hereinafter), preferably 10.0 to 30.0 %, of component (A). When the content of component (A) is less than 1.0%, the effects of the present invention cannot be achieved. When it exceeds 50.0 %, on the other hand, the resulting system becomes unstable.

Examples of the cationic surfactant to be used as component (B) in the present invention include quaternary ammonium salts, alkylpyridinium salts, alkylmorpholinium salts, alkylisoquinolinium salts, alkylimidonium salts, alkylamine salts and alkylamideamine salts.

Among these cationic surfactants, quaternary ammonium salts containing at least one alkyl group having 8 to 28 carbon atoms are preferable. Examples thereof include quaternary ammonium salts of the following formulae (II) and (III):

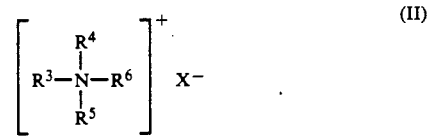

(II)

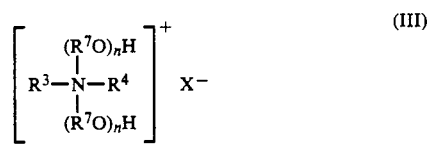

(III)

wherein at least one of $R^3$, $R^4$, $R^5$ and $R^6$ represents an alkyl group or an alkenyl group, which may be substituted with an alkoxy group, an alkenyloxy group, an alkanoylamino group or an alkenoylamino group, where the total number of carbon atom is 8 to 28, while the others, if not such an alkyl or alkenyl group, each represent a benzyl group or an alkyl group having 1 to 5 carbon atoms or a hydroxyalkyl group having 1 to 5 carbon atoms, $R^7$ represents an alkylene group having 2 or 3 carbon atoms, X represents a halogen ion or an organic anion and n is an integer of from 1 to 20.

The quaternary ammonium salts represented by formulae (II) and (III) may be synthesized in a conventional manner as disclosed, for example, in the above mentioned *Kesyohin Genryo Kijun*.

Among these quaternary ammonium salts, a quaternary ammonium salt of formula (II) is preferable. More preferable examples of the quaternary ammonium salts of formula (II) include branched quaternary ammonium salts of the following general formula (IV) to (VI):

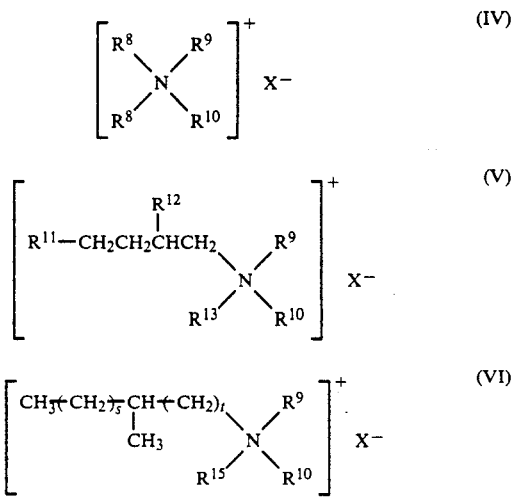

wherein $R^8$ represents (a) a branched alkyl group of the formula:

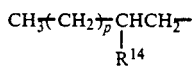

wherein $R^{14}$ represents a methyl group or an ethyl group and p is an integer which will give $R^8$ a total carbon atom number of from 8 to 16 and/or (b) a straight chain alkyl group of the formula: $CH_3CH_2(CH_2)_q$ wherein q is an integer of from 7 to 15), $R^9$ and $R^{10}$ each represent a benzyl group or an alkyl group having 1 to 3 carbon atoms or a hydroxyalkyl group having 1 to 3 carbon atoms, $R^{11}$ and $R^{12}$ each represent an alkyl group having 2 to 12 carbon atoms, $R^{13}$ represents a group represented by the formula:

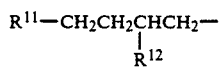

or an alkyl group having 1 to 3 carbon atoms, where $R^{11}$ and $R^{12}$ are as earlier defined, $R^{15}$ represents a group represented by the formula:

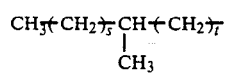

or an alkyl group having 1 to 3 carbon atoms, s is an integer of from 2 to 14, t is an integer of from 3 to 11, provided that s+t is from 9 to 21, X− is a halogen ion or an organic anion, and the branching ratio ((a)/(a)+(b)) in the quaternary ammonium salt(s) represented by formula (IV) is from 10 to 100 % by mol as a whole.

The branched quaternary ammonium salt(s) represented by formula (IV) may be synthesized, for example, from an oxoalcohol having 8 to 16 carbon atoms in a conventional manner as described in the above mentioned *Kesyohin Genryo Kijun*. Examples thereof include dialkyldimethylammonium salts, dialkylmethylhydroxyethylammonium salts and dialkylmethylbenzylammonium salts each having an alkyl group derived from an oxoalcohol.

As the quaternary ammonium salt(s) of formula (IV), those having the branching ratio as earlier defined of from 10 to 100 % as a whole is usually employed in the present invention. In the present invention, one quaternary ammonium salt of formula (IV) may have one or two of the substituent (a) for $R^8$ and another quaternary ammonium salt of formula (IV) may have one or two of the substituent (b) for $R^8$, provided that the mixture thereof as a whole suffices to the branching ratio as earlier defined.

It is particularly preferable to use those having a branching ratio as earlier defined of from 10 to 50 %. In the present invention, the total number of carbon atoms in the $R^8$ group may range from 8 to 16. It is preferable to use such quaternary ammonium salts having a specific distribution. It is more preferable to use those having the following distribution:

$C_8$–$C_{11}$: 5% by mol or less,
$C_{12}$: 10–35% by mol,
$C_{13}$: 15–40% by mol,
$C_{14}$: 20–45% by mol,
$C_{15}$: 5–30% by mol and
$C_{16}$: 5% by mol or less, total being 100%.

Specific examples of such quaternary ammonium salts include dialkyldimethylammonium chloride carrying alkyl groups having 8 to 16 carbon atoms and having a branching ratio as earlier defined of from 10 to 50 %.

The branched quaternary ammonium salts represented by formula (V) may be synthesized in a conventional manner from a Guerbet alcohol

where $R^{11}$ and $R^{12}$ are as earlier identified) having 8 to 28 carbon atoms. Preferable examples of the branched quaternary ammonium salt include alkyltrimethylammonium salts, alkyldimethylbenzylammonium salts, dialkyldimethylammonium salts, dialkylmethylhydroxyethyl ammonium salts and dialkylmethylbenzylammonium salts, each having an alkyl group derived from a Guerbet alcohol. Among these substances, 2-decyltetradecyltrimethylammonium chloride, 2- dodecylhexadecyltrimethylammonium chloride, di-2- hexyldecyldimethylammonium chloride and di-2-octyldodecyl-dimethylammonium chloride are particularly preferable.

As the methyl branched quaternary ammonium salt represented by formula (VI), those wherein s +t is 15 are preferable.

The methyl branched quaternary ammonium salt represented by formula (VI) may be synthesized by the manner described, for example, in *The fifteenth IFSCC*

*International Congress* (1988), *Preprints*, vol.1, pages 71 to 87.

Examples of the counter ion X— in the quaternary ammonium salts represented by formulae (II), (III), (IV), (V) and (VI) include halogen ions (for example, chlorine, iodine, bromine ions); and organic anions (for example, methosulfate, ethosulfate, methophosphate, ethophosphate).

The hair cosmetic of the present invention may contain 0.01 to 20.0 %, preferably 0.2 to 10.0 %, of component (B). When the content of component (B) in the hair cosmetic of the present invention is less than 0.01 %, the effects of the invention cannot be achieved. When it exceeds 20.0 %, on the other hand, the resulting product shows an undesirable oily feel.

The term hair cosmetic composition as used herein includes all cosmetics to be applied to the hair, for example, a pre-shampoo, shampoo, hair rinse, hair conditioner, hair treatment, set lotion, blow styling lotion, hair spray, styling foam, styling gel, hair liquid, hair tonic, hair cream, permanent waving first solution, permanent waving second solution, permanent hair dye and temporary hair dye.

It may be formulated into various forms depending on the purpose, for example, an aqueous solution, an ethanolic solution, an emulsion, a suspension, a gel, a liquid crystals, a solid, an aerosol, etc.

In addition to the above-mentioned essential components, the hair cosmetic composition of the present invention may further contain various components commonly used in the art.

The hair cosmetic of the present invention may contain one or more components selected from anionic surfactants (for example, alkyl benzensulfonates, alkyl ether sulfates, olefin sulfonates, α-sulfofatty acid esters, amino acid surfactants, phosphate surfactants, sulfosuccinate surfactants); ampholytic surfactants (for example, sulfonate surfactants, betaine surfactants, alkylamine oxide surfactants, imidazoline surfactants); and nonionic surfactants (for example, polyoxyethylene alkyl ethers, polyoxyethylene alkyl phenyl ethers, alkanolamides, alkylene oxide adducts thereof, esters of polyhydric alcohols and fatty acids, sorbitan fatty acids, and alkyl saccharide surfactants) depending on the performance of the desired hair care product. When the hair cosmetic composition of the present invention is to be formulated into a shampoo, it is particularly preferable to use amino acid surfactants, phosphate surfactants, α-sulfofatty acid esters, imidazoline surfactants, alkyl saccharide surfactants and sulfosuccinate surfactants, among the above mentioned ones, as the major detergent component, taking irritation to the skin and hair into consideration.

The hair cosmetic of the present invention may contain 0.01 to 40.0 %, preferably 0.05 to 20.0 %, of surfactant(s) other than component (B).

In order to improve the texture of the hair or skin, the hair cosmetic of the present invention may further contain one or more components selected from among cationic polymers, for example, cationized cellulose derivatives, cationic starch, cationized guar gum derivatives, diallyl quaternary ammonium salt/acrylamide copolymers, quaternary polyvinyl pyrrolidone derivatives, and polyglycol polyamine condensation products.

Preferable examples of these cationic polymers include cationized cellulose having a molecular weight of from about 100,000 to 3,000,000 (M.W.), cationized starch having a degree of cationization of from about 0.01 to 1, cationized guar gum having a degree of cationization of from about 0.01 to 1 (e.g., JAGUAR, trade name, manufactured by Celanese Co.), a diallyl quaternary ammonium salt/acrylamide copolymer having a molecular weight of from about 30,000 to 2,000,000 (M.W.), a quaternaized product of polyvinyl pyrrolidone/dimethylaminoethylmethacrylate copolymer having a molecular weight of from 10,000 to 2,000,000 (M.W.) and having a cationic nitrogen content in the vinyl polymer of from 1.8 to 2.4 %, a polyglycol polyamine condensation product having an alkyl group having 6 to 20 carbon atoms, an adipic acid/dimethylaminohydroxypropyldiethylenetriamine copolymer (e.g., CARTERETIN, trade name, manufactured by Sandz Co.) and cationic polymers as disclosed in JP-A-53-139734 (the term "JP-A" as used herein means an "unexamined published Japanese Patent Application") (corresponding to U.S. Pat. No. 4,240,450) and JP-A-60-36407 (corresponding to U.S. Pat. No. 4,597,962).

The hair cosmetic of the present invention may contain from 0.05 to 20.0 %, preferably from 0.1 to 10.0 %, based on the total weight of the composition, of the cationic polymer.

To further improve the texture of the hair or skin, the hair cosmetic of the present invention may contain one or more silicone derivatives selected from among dimethyl polysiloxane, methylphenyl polysiloxane, amino-denatured silicone, fatty acid-denatured silicone, alcohol-denatured silicone, aliphatic alcohol-denatured silicone, polyether-denatured silicone, epoxy-denatured silicone, fluorine-denatured silicone, cyclic silicone, alkyl-denatured silicone. Each silicone derivative may be used either alone or in the form of a latex composition obtained through emulsion polymerization according to the method described in for example, JP-B-56-38609 (the term "JP-B" as used herein means an "examined Japanese Patent Publication").

Among these silicone derivatives, dimethyl polysiloxane (degree of polymerization: 500 or more), polyether-denatured silicone, amino-denatured silicone and cyclic silicone are particularly preferable in order to impart a excellent texture to the hair.

The hair cosmetic of the present invention may contain 0.01 to 20.0 %, preferably 0.05 to 10.0 %, based on the total weight of the composition, of the silicone derivative.

The hair cosmetic of the present invention may further arbitrarily contain various components commonly used in the art, for example, texture improvers (for example, higher fatty acid salts alkylamine oxides, fatty acid alkanol amides, squalane, lanolin); humectants (for example, propylene glycol, glycerol, sorbitol, amide derivatives represented by following formula (VII):

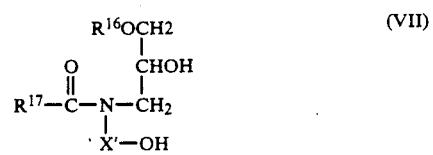

wherein $R^{16}$ represents a straight-chain or branched, saturated or unsaturated hydrocarbon group having 10 to 26 carbon atoms, $R^{17}$ represents a straight-chain or branched, saturated or unsaturated hydrocarbon group having 9 to 25 carbon atoms and X' represents a —$(CH_2)_m$— group (wherein m is an integer of from 2 to 6)); viscosity controlling agents (for example, methyl cellulose, carboxyvinyl polymers, hydroxyethyl cellulose, polyoxyethylene glycol distearate, ethanol); pearling agents; perfumes; colorants, UV absorbers; antioxidants; bactericides (for example, triclosan, trichlorocarbane); antiinflammatory agents (for example, potassium glycyrrhizinate, tocopherol acetate); antidandruff agents (for example, zinc pyrithione, octopyrox); and preservatives (for example, methylparaben, butylparaben), so long as the effects of the invention are not deteriorated thereby.

The hair cosmetic of the present invention may be preferably adjusted to a pH of 3 to 10, more preferably a pH of 4 to 8, with the use of an acid or alkali as commonly used in hair cosmetics.

The hair cosmetic of the present invention imparts an excellent touch to the hair without showing any stickiness or oily feel and effectively protects the hair from splitting or breaking.

To further illustrate the present invention, and not by way of limitation, the following Examples are given. Unless otherwise specified, all percentages are by weight.

EXAMPLE 1

A shampoo product of the composition as given in Table 1 was prepared and its performance was evaluated. Table 1 shows the results.

Evaluation method:

(1) Approximately 20 g of the hair of a Japanese woman, which had never been permed nor bleached, about 15 to 20 cm in length, was bundled and moistened with warm water at about 40° C. Next, 1 g of the shampoo composition was uniformly applied to the hair and allowed to foam for one minute. Then the hair was rinsed with running water and dried. The softness, oily feel, moist feel and smoothness of the hair were evaluated based on the following criteria. Evaluation was conducted one by ten panelists and the results were expressed in the mean value thereof.

Softness
  A: Very soft.
  B: Soft.
  C: Neither hard nor soft.
  D: Hard.
Oily feel
  A: Very little.
  B: Little.
  C: Neither little nor serious.
  D: Serious.
Moist feel
  A: Very moist.
  B: Moist.
  C: Neither moist nor dry.
  D: Dry.
Smoothness
  A: Very smooth.
  B: Smooth.
  C: Neither smooth nor rough.
  D: Rough.

(2) Bundled hair treated in the same manner as the described in (1) was brushed and the degree of the formation of split hair was evaluated based on the following criteria.
  A: No increase in split hairs.
  B: Scarcely any increase in split hairs.
  C: Somewhat increase in split hairs.
  D: Obvious increase in split hairs.

As can be seen from the results shown in Table 1 below, the performance of the products of the invention are superior to that of the comparative products in almost evaluation items, especially in the evaluation items of softness, moist feel, smoothness and formation of split hair.

TABLE 1

| Component | Product of the Invention | | | | | | Comparative Product | | | |
|---|---|---|---|---|---|---|---|---|---|---|
| | 1 (%) | 2 (%) | 3 (%) | 4 (%) | 5 (%) | 6 (%) | 1 (%) | 2 (%) | 3 (%) | 4 (%) |
| polyoxyethylene (2.5 E.O.) sodium lauryl sulfate | 20 | — | — | — | — | 20 | — | 20 | 20 | 20 |
| polyoxyethylene (2.5 E.O.) triethanolamine lauryl sulfate | — | 20 | — | — | — | — | — | — | — | — |
| triethanolamine lauryl sulfate sodium | — | — | 20 | — | — | — | — | — | — | — |
| α-olefin sulfonate* | — | — | — | 20 | — | — | — | — | — | — |
| imidazoline surfactant** | — | — | — | — | 20 | — | — | — | — | — |
| lauric diethanolamide | 3 | 3 | 3 | 3 | 3 | 3 | 3 | 3 | 3 | 3 |
| dipropylene glycol monopropyl ether | 10 | 10 | 10 | 10 | 10 | 10 | — | — | — | 10 |
| N-(2-decyl)hexadecyl-N,N,N-trimethyl-ammonium chloride*** | 0.5 | 0.5 | 0.5 | 0.5 | 0.5 | — | — | 0.5 | — | — |
| stearyltrimethylammonium chloride | — | — | — | — | — | 0.5 | — | — | 0.5 | — |
| purified water | Balance | Balance | Balance | Balance | Balance | Balance | Balance | Balance | Balance | Balance |
| total | 100 | 100 | 100 | 100 | 100 | 100 | 100 | 100 | 100 | 100 |
| Softness | B | B | B | B | B | B | D | D | D | C |
| Oily feel | B | B | B | B | B | B | B | C | D | B |
| Moist feel | B | B | B | B | A | B | D | D | D | C |
| Smoothness | A | A | A | A | A | B | D | C | C | D |
| Formation of split hair | A | A | A | A | A | B | D | C | C | C |

Notes;
*Sodium tetradecenesulfonate.
**Miranol C2M conc. (sodium salt of secondary amide imidazoline surfactant derived from coconut fatty acids, manufactured by Miranol Chemical Co.)
***Synthesized from Guerbet alcohol (Enudicol 240 A, manufactured by Shin Nippon Rika).

EXAMPLE 2

A hair treatment product of the composition as given in Table 2 was prepared and its performance was evaluated. Table 2 shows the results.

Evaluation method:

Approximately 20 g of the hair of a Japanese woman, which had never been permed nor bleached, about 15 to 20 cm in length, was bundled and washed with a shampoo. Next, 2 g of the hair treatment product was uniformly applied to the hair and the hair then rinsed with running water for 30 minutes. After drying with a towel, the hair was dried with a drier and the hair under dry condition was evaluated. The same criteria as employed in Example 1 were used.

As can be seen from the results shown in Table 2 below, the products of the invention exhibit markedly improvements in the effect to hair, especially in evaluation items of softness, oily feel, moistness and formation of split hair.

TABLE 2

| Component | Product of the Invention | | | Comparative Product | |
|---|---|---|---|---|---|
| | 7 (%) | 8 (%) | 9 (%) | 5 (%) | 6 (%) |
| stearyltrimethyl-ammonium chloride | — | 2 | 1 | 2 | 1 |
| N-(2-decyl)tetradecyl-N,N,N-trimethylammonium chloride | 2 | — | 1 | — | 1 |
| diethyleneglycol monoethyl ether | 20 | 20 | 20 | — | — |
| cetyl alcohol | 5 | 5 | 5 | 5 | 5 |
| N-(2-hydroxy-3-hexadecyloxypropyl)-N-2-hydroxyethylhexadecanamide | 3 | 3 | 3 | 3 | 3 |
| water | Balance | Balance | Balance | Balance | Balance |
| total | 100 | 100 | 100 | 100 | 100 |
| Softness | B | B | B | D | C |
| Oily feel | B | B | B | D | C |
| Moist feel | A | B | A | D | B |
| Smoothness | B | B | B | D | C |
| Formation of split hair | A | B | B | D | C |

EXAMPLE 3

Hair treatment products of the composition as given in Table 3 were prepared and their performance was evaluated in the same manner as the one described in Example 2. Table 3 shows the results.

TABLE 3

| Component | Product of the Invention | | | |
|---|---|---|---|---|
| | 10 (%) | 11 (%) | 12 (%) | 13 (%) |
| N-(2-decyl)tetradecyl-N,N,N-trimethylammonium chloride | 2 | 2 | 2 | 2 |
| diethylene glycol monoethyl ether | 5 | 20 | 30 | — |
| diethylene glycol monobutyl ether | — | — | — | 20 |
| cetyl alcohol | 5 | 5 | 5 | 5 |
| N-(2-hydroxy-3-hexadecyloxypropyl)-N-2-hydroxyethylhexadecanamide | 3 | 3 | 3 | 3 |
| water | Balance | Balance | Balance | Balance |
| total | 100 | 100 | 100 | 100 |
| Softness | B | B | A | B |
| Oily feel | B | B | B | B |
| Moist feel | B | A | A | A |
| Smoothness | B | B | A | B |
| Formation of split hair | B | A | A | A |

As can be seen from the results shown in Table 3 above, the hair treatment products according to the present invention exhibit superior performance by using each of these dialkylene glycol monoalkyl ether in each amount.

EXAMPLE 4

The product of the invention (7) obtained in Example 2 above and a comparative product (7) of the following composition were compared by 10 panelists regarding softness, oily feel, moist feel, smoothness and formation of split hair. As a result, the product of the invention (7) was preferred to the comparative one in all evaluation items at a ratio of 8:2 on average.

| Component | Content (%) |
|---|---|
| N-(2-decyl)tetradecyl-N,N,N-trimethyl-ammonium chloride | 2 |
| cetyl alcohol | 5 |
| N-(2-hydroxy-3-hexadecyloxypropyl)-N-2-hydroxyethylhexadecanamide | 3 |
| water | balance |

EXAMPLE 5

| Hair rinse composition | Content (%) |
|---|---|
| (1) N-(2-decyl)tetradecyl-N,N,N-trimethyl-ammonium chloride | 1.0 |
| (2) stearyltrimethylammonium chloride | 0.5 |
| (3) diethylene glycol monoethyl ether | 20.0 |
| (4) cetostearyl alcohol | 3.0 |
| (5) zinc pyrithione | 0.3 |
| (6) methylparaben | 0.2 |

-continued

| Hair rinse composition | Content (%) |
|---|---|
| (7) perfume | 0.4 |
| (8) deionized water | balance |
| Total | 100% |

EXAMPLE 6

| Styling lotion composition: | Content (%) |
|---|---|
| (1) N-(2-decyl)tetradecyl-N,N,N-trimethyl-ammonium chloride | 0.5 |
| (2) dipropylene glycol monoethyl ether | 20.0 |
| (3) acrylic resin alkanolamine solution (Plasize, trade name, manufactured by Goo Chemical Co.) | 5.0 |
| (4) polyethylene glycol (PEG 20,000, manufactured by Sanyo Kasei Co.) | 1.0 |
| (5) ethanol | 20.0 |
| (6) perfume | 0.3 |
| (7) water | balance |
| Total | 100% |

EXAMPLE 7

| Conditioning foam composition: | Content (%) |
|---|---|
| (1) N-(2-decyl)tetradecyl-N,N,N-trimethyl-ammonium chloride | 0.5 |
| (2) octyldodecyl myristate | 1.0 |
| (3) dipropylene glycol | 1.0 |
| (4) diethylene glycol monopentyl ether | 20.0 |
| (5) glycerol | 2.5 |
| (6) liquid paraffin (Hicol K-310, trade name, manufactured by Kaneda, Co.) | 2.5 |
| (7) polyoxyethylene sorbitan monostearate (Lheodol TW-S120, trade name, manufactured by Kao Corp.) | 0.2 |
| (8) ethanol | 5 |
| (9) methylparaben | 0.1 |
| (10) perfume | 0.1 |
| (11) propellant (LPG) | 10 |
| (12) water | balance |
| Total | 100% |

EXAMPLE 8

| Permanent waving first solution: | Content (%) |
|---|---|
| (1) ammonium thioglycolate | 6.0 |
| (2) aqueous ammonia | 3.0 |
| (3) Frost DS (disodium edetate) | 0.5 |
| (4) diethylene glycol monomethyl ether | 20.0 |
| (5) N-(2-decyl)tetradecyl-N,N,N-trimethyl-ammonium chloride | 2.0 |
| (6) water | balance |
| Total | 100% |

EXAMPLE 9

| Permanent waving second solution II: | Content (%) |
|---|---|
| (1) sodium borate | 8.0 |
| (2) N-(2-decyl)tetradecyl-N,N,N-trimethyl-ammonium chloride | 2.0 |
| (3) dipropylene glycol monoisopropyl ether | 20.0 |
| (4) water | balance |
| Total | 100% |

EXAMPLE 10

| Shampoo Composition: | Content (%) |
|---|---|
| (1) N-lauroyl-N'-carboxymethyl-N'-(2-hydroxyethyl)ethylenediamine TEA salt | 10 |
| (2) diethylene glycol monobutyl ether | 5 |
| (3) polyoxyethylene (5) disodium lauryl sulfosuccinate | 5 |
| (4) lauric diethanolamide | 2 |
| (5) coconut oil fatty acid amide propyl betaine (Softazoline, trade name, manufactured by Kawaken Fine Chemical Co., Ltd.) | 2 |
| (6) distearyldimethylammonium chloride | 0.1 |
| (7) cationized cellulose (Polymer JR400, trade name, manufactured by UCC Co.) | 0.15 |
| (8) perfume | 0.5 |
| (9) colorant | q.s. |
| (10) water | balance |
| Total | 100% |

While the invention has been described in detail and with reference to specific examples thereof, it will be apparent to one skilled in the art that various changes and modifications can be made therein without departing from the spirit and scope thereof.

What is claimed is:

1. A hair cosmetic composition consisting essentially of the following components (A) and (B):

(A) 1.0 to 50.0% by weight, based on the total weight of the composition, of a dialkylene glycol monoalkyl ether represented by the general formula (I):

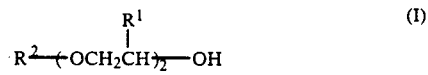

wherein $R^1$ represents a hydrogen atom or a methyl group and $R^2$ represents an alkyl group having 1 to 5 carbon atoms; and (B) 0.01 to 20.0% by weight, based on the total weight of the composition, of one or more cationic surfactants.

2. A hair cosmetic composition as claimed in claim 1, wherein said cationic surfactant is one or more compounds selected from quaternary ammonium salts represented by formulae (II) or (III):

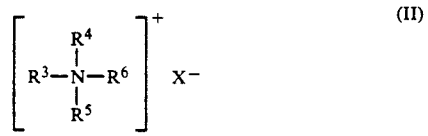

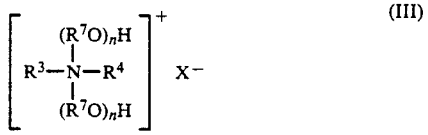

wherein at least one of $R^3$, $R^4$, $R^5$ and $R^6$ represents an alkyl group or an alkenyl group which may be substituted with an alkoxy group, an alkenyloxy group, an alkanoylamino group or an alkenoylamino group having 8 to 28 carbon atoms in total, while any of $R^3$, $R^4$, $R^5$ and $R^6$ which do not represent a group as defined above each represents each a benzyl group or an alkyl group or a hydroxyalkyl group having 1 to 5 carbon atoms, $R^7$ represents an alkylene group having 2 or 3 carbon atoms, X— represents a halogen ion or an organic anion and n is an integer of from 1 to 20.

3. A hair cosmetic composition as claimed in claim 1, wherein said cationic surfactant is one or more compounds selected from branched quaternary ammonium salts represented by formulae (IV), (V) or (V):

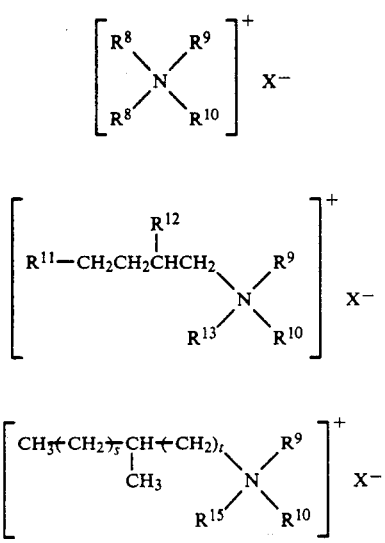

wherein $R^8$ represents (a) a branched alkyl group of the formula:

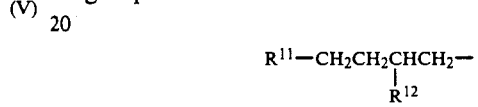

wherein $R^{14}$ represents a methyl group or an ethyl group and p is an integer giving $R^8$ a total number of carbon atom of from 8 to 16 or $R^8$ represents (b) a straight chain alkyl group of the formula: $CH_3$—$(CH_2)_q$— wherein q is an integer of from 7 to 15, with the proviso that the ratio of (a) to (b) in the groups represented by $R^8$ meets the requirement that the branching ratio ((a)/(a)+(b)) in the quaternary ammonium salt(s) represented by formula (IV) is from 10 to 100% by mol as a whole, $R^9$ and $R^{10}$ each represent a benzyl group or an alkyl group or a hydroxylakyl group having 1 to 3 carbon atoms, $R^{11}$ and $R^{12}$ each represent an alkyl group having 2 to 12 carbon atoms, $R^{13}$ represents a group of the formula:

$$R^{11}-CH_2CH_2\underset{\underset{R^{12}}{|}}{C}HCH_2-$$

or an alkyl group having 1 to 3 carbon atoms, $R^{15}$ represents a group of the formula:

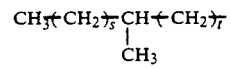

or an alkyl group having 1 to 3 carbon atoms, s is an integer of from 2 to 14 and t is an integer of from 3 to 11, provided that s +t is from 9 to 21, and X— is a halogen ion or an organic anion.

* * * * *